United States Patent [19]

Kupiecki et al.

[11] Patent Number: 5,669,931

[45] Date of Patent: Sep. 23, 1997

[54] LIQUID COILS WITH SECONDARY SHAPE

[75] Inventors: David Kupiecki, Cupertino; Cong Thach, Fremont; John E. Ortiz, East Palo Alto; Neil J. Sheehan, Palo Alto, all of Calif.

[73] Assignee: Target Therapeutics, Inc., Fremont, Calif.

[21] Appl. No.: 624,669

[22] Filed: Apr. 2, 1996

Related U.S. Application Data

[63] Continuation-in-part of Ser. No. 413,970, Mar. 30, 1995.

[51] Int. Cl.$^6$ ............................................. A61B 17/12
[52] U.S. Cl. ......................................... 606/191; 606/198
[58] Field of Search ............................ 606/191, 198, 606/200, 195, 108; 604/53, 104

[56] References Cited

U.S. PATENT DOCUMENTS

| | | | |
|---|---|---|---|
| 3,452,742 | 7/1969 | Muller . | |
| 4,850,960 | 7/1989 | Grayzel | 604/53 |
| 4,994,069 | 2/1991 | Ritchart | 606/191 |
| 5,122,136 | 6/1992 | Guglielmi et al. | 606/32 |
| 5,133,731 | 7/1992 | Butler et al. | 606/191 |
| 5,139,243 | 8/1992 | Balsells . | |
| 5,217,484 | 6/1993 | Marks | 606/200 |
| 5,256,146 | 10/1993 | Ensminger et al. | 604/104 |
| 5,304,142 | 4/1994 | Liebl et al. | 606/191 |
| 5,312,415 | 5/1994 | Palermo | 606/191 |
| 5,334,210 | 8/1994 | Gianturco | 606/195 |
| 5,336,205 | 8/1994 | Zenzen et al. | 604/280 |

FOREIGN PATENT DOCUMENTS

WO 94/10936  5/1994  WIPO .

*Primary Examiner*—Michael Buiz
*Assistant Examiner*—Patrick W. Rasche
*Attorney, Agent, or Firm*—Morrison & Foerster LLP

[57] ABSTRACT

An occlusive implant includes an elongated member having an end, a portion proximal to that end, and a portion distal to that end. The proximal portion is sufficiently flexible so that it can be folded upon itself and maintain that configuration without further restraint. At least a portion of the distal portion is preformed to have a first configuration when in a first state and a second configuration when in a second state. The distal portion second configuration has a flow resistance substantially greater than that of the proximal portion. When discharged in the region to be occluded, the proximal portion is forced into a mass around at least a portion of the distal portion secondary structure. As the mass builds in size, it is believed to frictionally engage the surrounding vasculature wall and anchor the implant thereto. The occlusive implant preferably is provided in an introducer cartridge for delivery in vivo.

36 Claims, 3 Drawing Sheets

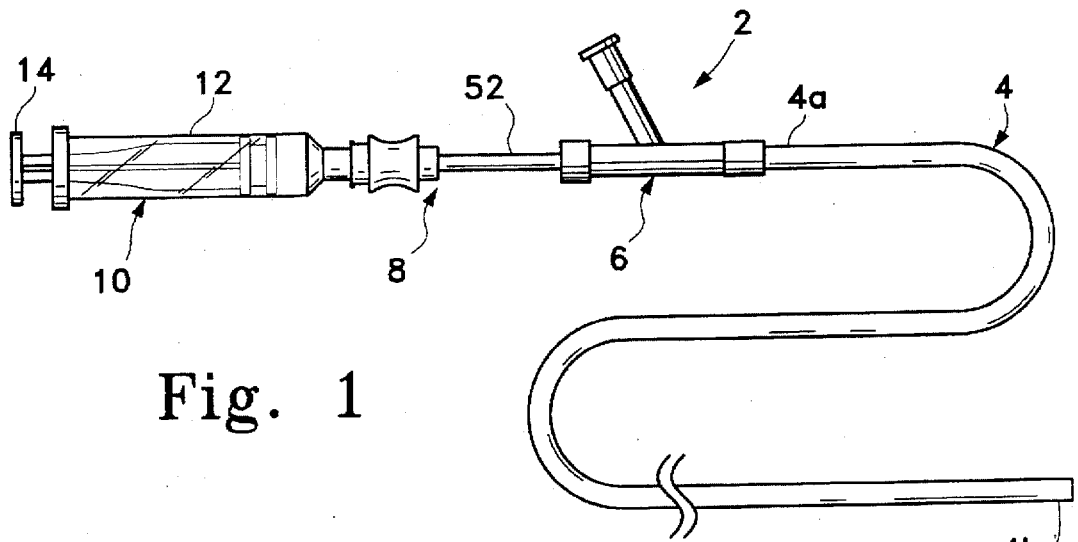
Fig. 1
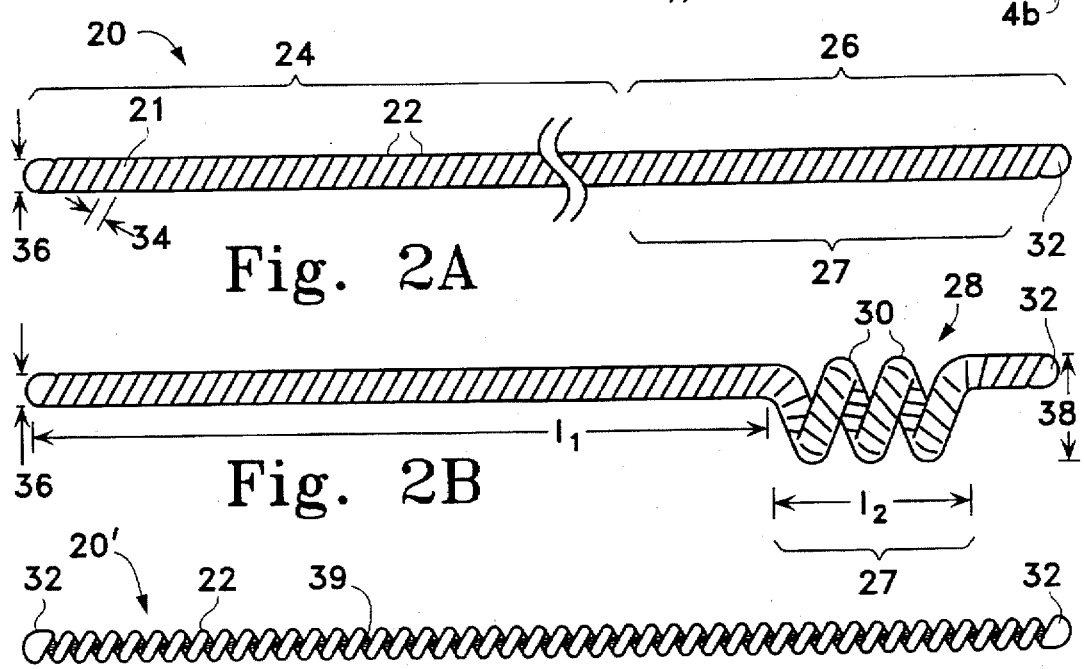
Fig. 2A
Fig. 2B
Fig. 2C
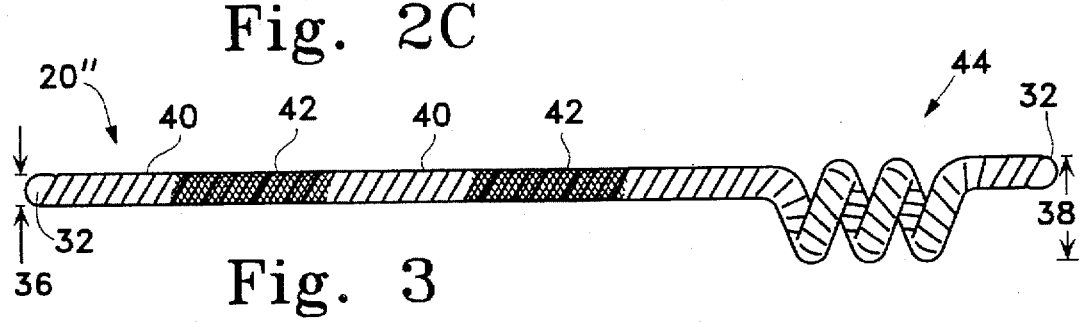
Fig. 3

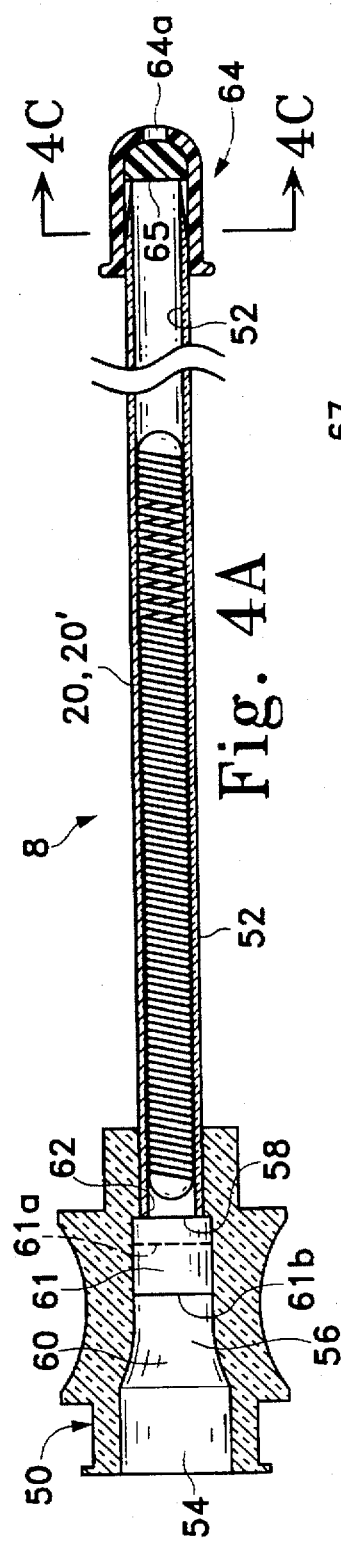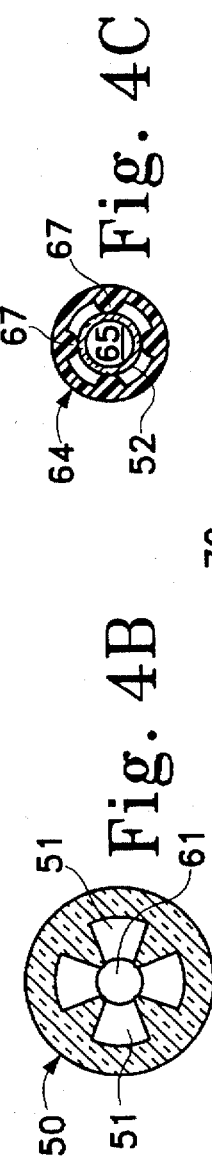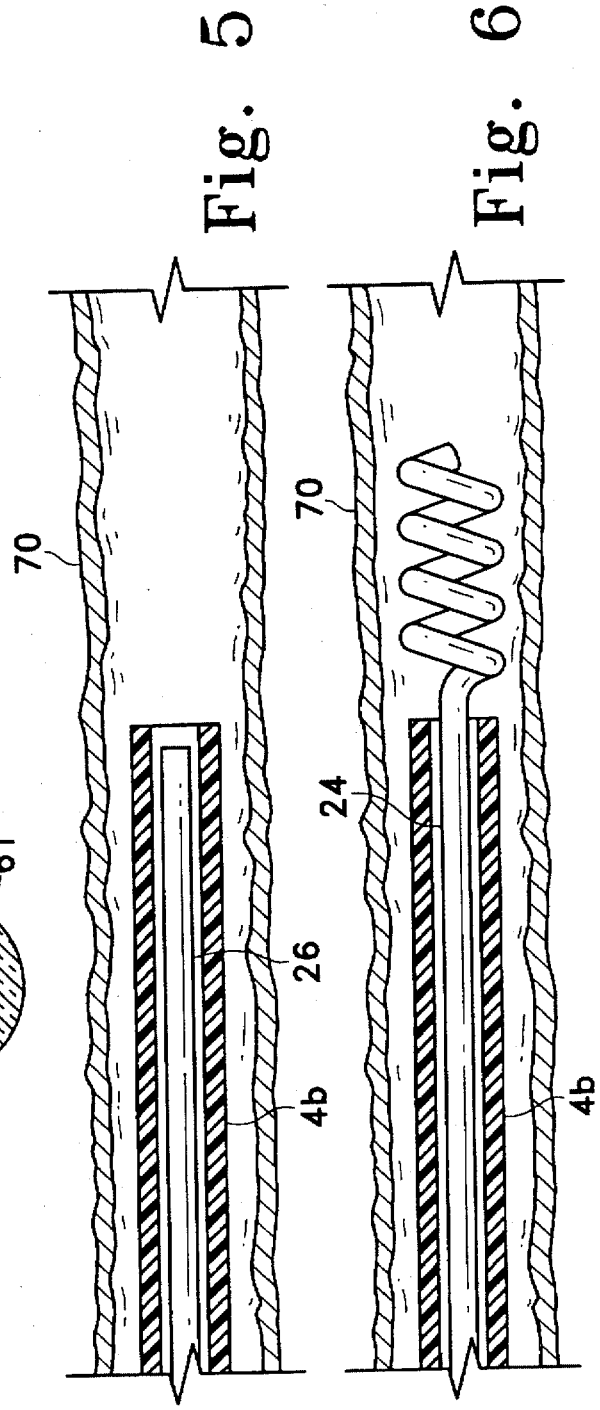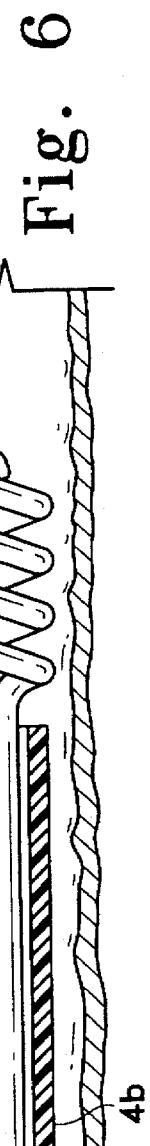

LIQUID COILS WITH SECONDARY SHAPE

CROSS-REFERENCES TO RELATED APPLICATIONS

This application is a continuation-in-part of Ser. No. 08/413,970 filed on Mar. 30, 1995.

FIELD OF THE INVENTION

The present invention relates to occlusive implants generally. More specifically, the invention involves occlusive implants, such as embolic coils, constructed with varying flow resistance characteristics to facilitate anchoring during hydraulic delivery, and methods of delivery.

BACKGROUND OF THE INVENTION

Endovascular therapy has been used in treating a variety of different conditions, including control of internal bleeding, occlusion of blood supply to tumors, and relief of vessel wall pressure in the region of an aneurysm. A variety of different embolic agents are known as arguably suitable for such therapy.

One known embolic agent includes injectable fluids or suspensions, such as microfibrillar collagen, various polymeric beads, and polyvinyl alcohol foam. The polymeric agents may be additionally crosslinked, sometimes in vivo, to extend the persistence of the agent at the desired vascular site. These agents are often introduced into the vasculature through a catheter. After such introduction, materials there form a solid space-filling mass. Although they provide good short-term vaso-occlusion, they are ultimately reabsorbed in the process of vessel recanalization.

Polymer resins, typically cyanoacrylates, are also employed as injectable vaso-occlusive materials. The resins are typically mixed with a radio-opaque contrast material or made radiopaque by the addition of tantalum powder. However, placement of the mixture is quite difficult. Inadvertent embolisms in normal vasculature (due to the inability of controlling the destination of the pre-gelled resins) is not altogether uncommon. The material is impossible to retrieve once it has been placed in the vasculature. Such resins have not been FDA approved, and a waiver must be requested in each instance where the materials are applied during human operative procedures.

A number of mechanical vaso-occlusive devices are widely used. One such device is a balloon which may be carried to the vessel site at the end of the catheter and there inflated with a suitable fluid, typically a polymerizable resin, and released from the end of the catheter. The balloon device has the advantage that it effectively fills the cross-section of the occluded vessel. However, when using intravascular balloon embolization of intracranial berry aneurysms, inflation of a balloon into the aneurysm carries some risk of aneurysm rupture due to possible "overfilling" of portions of the sac and due to the traction produced when detaching the balloon from the end of the catheter. Moreover, a vascular balloon is difficult to retrieve after the resin within the balloon sets up, and the balloon cannot be easily visualized using radiographic techniques unless it is filled with contrast material. Balloons have also been known to rupture during filling, or release prematurely during filling, or leak monomeric resin into the vasculature during the period before the monomer sets up into polymeric form.

Another type of mechanical vaso-occlusive device is a wire coil or braid which can be introduced through a catheter in a stretched linear form and which assumes an irregular shape upon discharge of the device from the end of the catheter. A variety of vaso-occlusive coils and braids are known. For instance, U.S. Pat. No. 4,994,069, to Ritchart et al., shows a flexible, preferably coiled, wire for use in small vessel vaso-occlusion. Unlike vaso-occlusive coils previously, Ritchart et al. teaches a coil which is fairly soft and is delivered to the site using a pusher within a catheter lumen. The Ritchart et al. coils are typically pushed into the desired vascular site in a linear configuration. Upon discharge from the catheter, the coil may undertake any of a number of random or regular configurations designed to fill the site. The coils are used for small vessel sites, e.g., 0.5–6.0 mm in diameter. The coils themselves are said to be between 0.010 and 0.030 inches in diameter. The length of the coiled wire is typically 15–20 times the diameter of the vessel to be occluded. The wire used to make up the coils may be 0.002 to 0.006 inches in diameter. Tungsten, platinum and gold threads or wires are said to be preferred. These coils have a variety of benefits, including the fact that they are relatively permanent, they can be easily imaged radiographically, they may be located at a well-defined vessel site, and they can be retrieved.

A variation of the mechanical endovascular coil is the electrolytically detached endovascular coil described in U.S. Pat. No. 5,122,132 to Guglielmi et al. These coils are typically used in intracranial aneurysms because of their effectiveness in quickly forming controlled emboli. The disclosed coils are similar to those of Ritchart et al. (supra) in size and in composition. However, the method of introducing the coil to the vascular site is somewhat different. Rather than mechanically thrusting the coil into the chosen site, the coil is placed at the site and a small voltage is applied to the guidewire supporting the coil so that the coil is electrolytically detached from the distal tip of the guidewire. The step of electrolytically detaching the coil has the added benefit of forming a thrombus as the coil is detached. Again, as noted above, the Guglielmi coils may be stainless steel or platinum or the like, and are typically 0.010 to 0.020 inches in diameter and are made using wire having approximate diameters of 0.001 to 0.005 inches. The coils in this service are typically between 1 and 50 centimeters in length.

There is a need for a liquid coil type fluid delivery embolism forming device that can be delivered to a particular site and anchored thereto.

SUMMARY OF THE INVENTION

The present invention provides an occlusive implant device comprising an elongated member having an end, a portion proximal to the end, and a portion distal to the end. The proximal portion is sufficiently flexible so that it can be folded upon itself and maintain that configuration without further restraint. At least a portion of the distal portion is preformed to have a first configuration when in a first state and a second configuration when in a second state. The distal portion second configuration has a flow resistance substantially greater than that of the proximal portion. With this construction, the proximal portion can be forced or accelerated toward the distal portion as the proximal portion is generally forced downstream to the occlusion site. The flexible aspect of the proximal portion facilitates its folding into a ball-like mass as it moves toward and piles against the distal portion. As the mass builds in size, it is believed to frictionally engage the surrounding vasculature wall and anchor the implant thereto. The distal portion secondary configuration may be such so as to engage the surrounding vasculature wall for anchoring the device prior to or at the same time the proximal portion engages the vasculature.

The extremely flexible proximal portion further facilitates achieving very high packing densities which improves occlusion rates. The flexibility of the device also facilitates removal of the implant with a syringe or retriever.

According to a preferred embodiment, the implant is hydraulically delivered. This facilitates delivery through soft flow directed catheters. In addition, the hydraulic delivery improves delivery speed through tortuous anatomy.

According to a further embodiment of the invention, the occlusive implant is provided in an introducer cartridge prior to delivery in vivo. In a preferred embodiment, the introducer cartridge generally includes a first portion having a passage formed therethrough for containing the implant and a second portion having a recess adapted for receiving fluid to eject the implant from the first portion passage into a delivery catheter, for example. According to one aspect of the inventive introducer cartridge, a blocking member is provided in the second portion recess adjacent to the passage. The blocking member preferably is constructed so that fluid can be discharged therethrough for impelling the implant through the catheter while the implant is blocked from backing into the recess. This is especially advantageous where a transition between the recess and passage, for example, may make it difficult or impossible to return the implant to the ejection passage without damaging it.

According to a preferred embodiment of the introducer cartridge, the blocking member comprises porous plastic. It has been found that porous plastic can provide an implant blocking filter that minimizes or eliminates snagging between the implant and filter. A cap may be coupled to the introducer cartridge outlet. The cap is constructed to facilitate the removal of air from the introducer cartridge without permitting implant discharge prior to use.

The above is a brief description of some of the features and advantages of the present invention. Other features, advantages and embodiments of the invention will be apparent to those skilled in the art from the following description, accompanying drawings and appended claims.

BRIEF DESCRIPTION OF THE DRAWINGS

FIG. 1 is a diagrammatic view of a hydraulic delivery system for delivering an occlusive device in accordance with the principles of the present invention.

FIG. 2A is a side view of an occlusion device constructed according to the present invention and showing the device as if it were in a radially restrained state.

FIG. 2B is a further view of the occlusion device of FIG. 2A showing the device in a relaxed state.

FIG. 2C is a side view of the coil of FIG. 2A with increased pitch and a thrombogenic bundle positioned therein.

FIG. 3 is a side view of another embodiment of the occlusion device of the present invention showing the device in a relaxed state.

FIG. 4A is a longitudinal section of a preferred introducer cartridge according to the present invention with the occlusive device of FIG. 2A positioned therein.

FIG. 4B is a transverse section of a variation of the introducer cartridge hub shown in FIG. 4A.

FIG. 4C is a transverse section taken along line 4C—4C in FIG. 4A.

FIG. 5 is a sectional view of the catheter of FIG. 1 showing the occlusion device of FIG. 2 prior to ejection therefrom.

FIG. 6 is a further view of the catheter of FIG. 5 showing the occlusion device partially ejected.

DETAILED DESCRIPTION OF THE PREFERRED EMBODIMENTS

Figure 7:
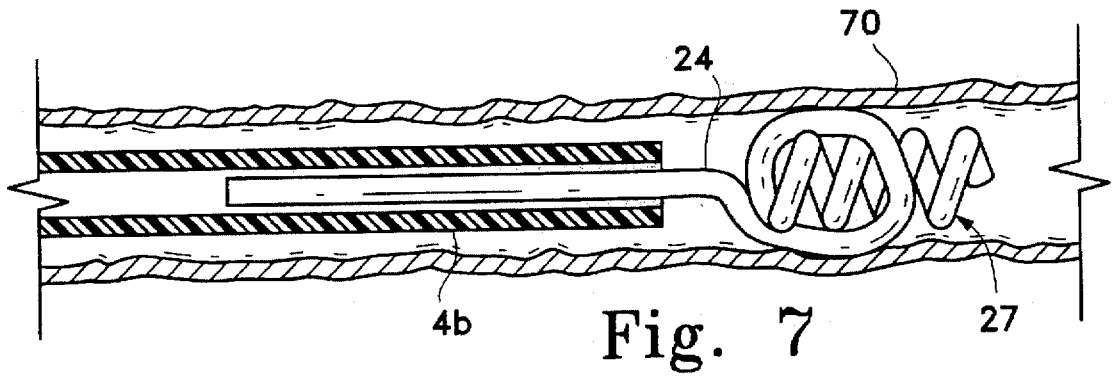
FIG. 7 is yet a further view of the catheter of FIG. 5 showing a later ejection stage with the occlusion device partially packed into an anchoring configuration.

Referring to the drawings in detail, wherein like numerals indicate like elements, occlusive implants or devices and preferred modes for their delivery are shown in accordance with the principles of the present invention.

The occlusive devices of the present invention generally are extremely flexible. The flexibility facilitates their reconfiguration at the selected site to form an occlusion or occlusion forming mass with minimal trauma to the site as will be described in more detail below.

In general, the devices are provided with a slender configuration for delivery to the selected site where they are balled up in a relatively dense occlusive mass having sufficient size to frictionally engage the interior walls of the lumen and anchor the device thereto. In the preferred embodiment, a hydraulic system is used to both deliver these devices, which are difficult to mechanically push due to their lack of significant column strength, and to reconfigure them into an occlusive mass.

Referring to FIG. 1, a catheter apparatus for hydraulically delivering occlusive devices of the present invention is shown. Apparatus 2 generally includes a catheter 4, an adapter or sidearm 6, introducer cartridge (or occlusive device cartridge) 8 and syringe 10. Sidearm 6, which is of conventional design for introducing fluids or apparatus to the catheter, fluidly couples the distal end of introducer cartridge 8 to the proximal end of the catheter. Syringe 10 is of conventional construction and includes a cylindrical barrel 12 and a plunger 14 that is reciprocally mounted therein.

Referring to FIGS. 2A and 2B, an occlusive implant or device 20 is shown constructed according to the present invention. In the illustrative embodiment, occlusive implant 20 comprises a coil. The coil is constructed so that it can assume a linear configuration (more specifically a rectilinear configuration) as shown in FIG. 2A and a compound linear and helical configuration as shown in FIG. 2B. The linear and compound configurations correspond to restrained and unrestrained coil shapes as will be discussed in more detail below.

Coil 20 preferably comprises a wire thread or filament 21 that is wound to form a primary coil structure having multiple windings 22 (primary windings). The coil generally includes a proximal portion 24 and a distal portion 26. At least a portion of distal portion 26 portion, designated with reference numeral 27, is formed to create a secondary coil structure 28. Secondary coil structure 28 has multiple windings 30 (secondary windings) as shown in FIG. 2B where the coil is depicted in a relaxed condition. The secondary windings may be described as being superposed on the primary windings.

Although secondary coil structure 28 is shown as a generally uniform diameter helix, other configurations can be used. For example, a helix having a progressively increasing or decreasing diameter from end to end (tapered helix) can be used. In addition, a helix having a varying diameter in the axial direction can be used. This includes, for example, a helix having its diameter progressively increase or decrease in both directions away from the center region of the helix. It also should be noted that secondary coil structure 28 can terminate at the distal extremity of occlusive device 20 or be spaced therefrom.

The generally rectilinear configuration shown in FIG. 2A is used in placing the coil at the desired site, for example, by advancing it through a catheter. When the coil is released from the catheter into the vessel, portion 27 assumes its secondary shape so that proximal portion 24 can be folded and intertwined therewith to form a relatively dense mass for occluding a vessel or forming an embolism. It is important that the occlusion device is extremely flexible so that it can be packed or folded into such a dense mass. The following physical characteristics have been found to provide the desired results.

The device flexibility is generally uniform throughout its length. The occlusive device also is constructed such that a one centimeter section or length of the device deflects more than about 20° under its own weight when one end of the section is supported and the other end is free or unrestrained. Most preferably that centimeter deflects at least 45°.

The flexibility can be achieved by using a wire (wire 21) having a diameter (diameter 34) of ≦0.001 inches (1 mil), in combination with a coil structure having minimal space between windings and a primary coil diameter of about 0.006 inches to 0.018 inches. However, it is believed that a wire diameter of ≦ about 0.002 inches (2 mil) also may provide suitable results. The ratio of space between windings to the wire diameter preferably is about 0 to 2:1. That is, the space between windings preferably is about 0 to 2 wire diameters. Thus, for a 1 mil diameter wire, for example, a suitable space size between adjacent turns is 0.001 inches, providing a total coil pitch of 0.002 inches. However, since increasing the space between windings increases flexibility, larger spaces can be provided and an equivalent flexibility achieved when using larger diameter wire (generally, the smaller the diameter of the wire the more flexible the coil). Minimal space between windings is preferred since a coil with large spaces may generate thrombic reactions in the catheter which, in turn, can result in sufficient friction to prevent effective flow of the occlusive device. The length of the coil generally may be between 5 mm and 80 cm, preferably is about 5 mm to 30 cm, but may be as small as 1 mm.

Occlusion device 20 can be formed by wrapping or winding fine filament or wire 21 about a spinning mandrel using well-known coil-manufacturing techniques. In manufacturing the coil, the winding process preferably is adjusted to produce a single-layer coil (i.e., a coil where the windings are close packed). That is, preferably, the windings are sufficiently close so that virtually no gap ( i.e., little or no gap) is formed between adjacent windings when it is placed in a straight, unstretched configuration (FIG. 1 ). The preferred pitch is about 0.001 to 0.004 inches, and more preferably about 0.001 to 0.003 inches, for a 1 mil diameter wire. In addition, the mandrel diameter is selected so that the outside diameter 36 of the primary windings 22 preferably will be in the range of about 0.006 to 0.018 inches.

The soft, flexible coil thus produced is cut to desired lengths after removal from the mandrel. Portion 27 of distal portion 26 of each cut length is then wound around a larger diameter mandrel to form helical winding 28. The mandrel is selected so as to form a secondary helical structure 28 including helical windings 30 with an outer diameter, indicated with reference numeral 38, that is preferably at least about 2 times the diameter 36 of primary windings 22, more preferably at least about 6 times diameter 36 and typically at least 10 times diameter 36. Diameter 38 preferably is about 0.040–0.120 inches (1.0–3.0 mm) and more preferably about 0.080–0.120 inches (2.0–3.0 mm). Proximal portion 24 may have an axial length ($l_1$) in the range of about 100–1200%, and typically about 100–500% of the axial length ($l_2$) of helical structure 28 to facilitate coil packing as will be described in more detail below. However, it is contemplated that other ratios also may be used.

After formation of the coil, its interior may be filled with a drug material and/or thrombogenic material such as a drug concentrate and its ends partially sealed for slow drug release from the coil in an in vivo aqueous environment. The ends of the coil may be sealed by a water-soluble plug for storage, if so desired. The coil may also (or alternatively) be coated with a thrombotic or medicinal material.

Alternatively, an end cap 32 may be included at one or both ends of coil 20. Cap 32 may be a separate piece or a fused portion of the coil or a bit of a filled material such as an epoxy. The major function of the end piece is to prevent the coil from catching on the interior of the catheter lumen or vessel. However, it is acceptable for devices of this size (the primary coil diameter is less than about 0.018 inches) to simply cut the coil ends and not use such an end cap.

Occlusive device 20 (and the variations described below) may be produced from any of a number of different materials. Some portion of the material preferably is radiopaque so that the coil and its position may be readily monitored within the human vasculature. Suitable materials include biocompatible metals, polymers, and alloys. For instance, biocompatible, radiopaque metals include silver, gold, palladium, platinum, tungsten, iridium, and various stainless steels. Other alloys such as platinum and tungsten (preferably 92% platinum and 8% tungsten) are suitable and, indeed, are often most preferred. The platinum-tungsten alloys desirably have a tensile strength of at least about 180 kpsi and, for a wire of a nominal 0.001 inch diameter, have a breaking load of 0.17 lb with a minimum elongation of 2% measured at a speed of 1.0 in/min. Various biocompatible polymers including polyethylene, polyurethane, polypropylene, and the like are suitable for use in these devices, but, because of their lack of radiopacity, must usually be teamed with a radiopaque marker or filled with a radiopaque filler to allow proper positioning of the coil within the body. Similarly, other inorganic materials such as fibrous carbon are suitable and may be used in the invention.

Although the windings shown in FIG. 2A have a generally uniform pattern, they may be arranged in an irregular pattern, e.g., one with varying pitch. In addition, although implant 20 is shown as coil-type implant, other constructions can be used. For example, a bundle 39 of thrombogenic fibers can be axially disposed in coil 20' as shown in FIG. 2C. Coil 20' is the same as coil 20 with the exception that coil 20' includes bundle 39 and preferably has more space between windings to expose the bundle to blood and, thus, enhance the device's thrombogenecity. Other configurations such as those disclosed in PCT publication no. WO 94/10936 (which is hereby incorporated herein by reference) can be used as well. For example, braid can be incorporated into the device as shown in FIG. 3.

Referring to FIG. 3, a combination coil-braid vaso-occlusive device 20" is shown according to the invention. Device 20" includes an alternating sequence of primary coils 40 and braid 42 and a secondary coil structure 44. Primary and secondary coils 40 and 44 are similar in construction to the primary and secondary coils described above. Lengths of the various coils 40 and braids 42, which are preferably 2 mm to 20 cm in length, are joined together at their respective ends to form the device. In another variation, the braid can be woven on the exterior of the coil. In a further embodiment, the coils may be formed as a double helix coil.

Each of the variations discussed above, when provided in the proper size range and materials, is an extremely soft and flexible device. These devices exert little if any radial force on the blood vessels into which they are placed. The fluid-like properties of the device enables it to conform to the complex geometry of certain fragile, abnormal blood vessels, and in so doing, minimize the risk of causing trauma to or even perforation of those blood vessels. Such flow properties also enable placement of the inventive device at sites in the vasculature currently unreachable by catheterization, such as those within an arteriovenous malformation (AVM).

As apparent from the foregoing, the occlusive implants exhibit relatively little column strength. Accordingly, they preferably are hydraulically delivered to the desired site as opposed to being mechanically pushed. A preferred introducer cartridge for introducing an occlusive device of the present invention is shown in longitudinal cross-section in FIG. 4A.

Referring to FIG. 4A, introducer cartridge 8 generally includes a hub 50 for receiving the discharge end of a syringe, such as syringe 10, and flexible, elongated tubular member 52 for discharging the occlusive device packaged therein into the catheter. In the illustrative embodiment, hub 50 is formed with first, second and third cylindrical recesses 54, 56 and 58, respectively. Recess 54 is configured to frictionally engage the discharge end (not shown) of syringe 10. Hub 50 may be configured with a conventional Luer or Luer lock fitting to mate with the discharge end of the syringe, for example. Recess 54 is fluidly coupled to smaller diameter recess 56 through tapered or conical region 60, and recess 56 is fluidly coupled to recess 58, which has a smaller diameter than recess 56. Recess 56 preferably contains an occlusive device blocking member, which may comprise a membrane or filter (such as a porous polymer type filter), for example, for permitting the working fluid (which preferably is a saline solution) to be discharged therethrough for impelling the occlusive device through the catheter, while blocking or preventing the occlusive device from backing into the hub. Such a blocking member is shown and designated with reference numeral 61 in FIG. 4A. Although the blocking member may have a relatively small axial dimension as indicated with dashed line 61a, this dimension may be larger as indicated with line 61b to facilitate placing the blocking member in the hub.

Blocking member 61 preferably comprises a filter generally having a flow resistance that facilitates forward fluid flow therethrough and minimizes the risk of filter displacement from the position shown in FIG. 4A when negative pressure (or fluid flow in the proximal direction) occurs. One material that has been found to provide desirable results is a high density porous plastic, and more particularly UHMW 1900, an ultra high molecular weight polyethylene commercially available from Himont, Inc. (N.J.). In this example, the material also preferably has a porosity in the range of about 50μ to 100μ, more preferably 60–80μ and most preferably about 70μ. Typically, filter 61 may be from about 0.10 to 0.20 inches in length, most preferably about 0.15 inches in length with a diameter of 0.125 inch when used with an introducer cartridge having a 0.120 inch inner diameter in the vicinity of recess 56, a combined axial dimension for recesses 54 and 56 of about 0.8 inch and about a 0.017–0.025 inch inner diameter tubular member 52 although differently sized tubular members are contemplated to be used as well. It should be understood that other materials such as sintered metal or polymer foam, for example, may be used to construct the blocking member as would be apparent to one of ordinary skill. However, porous plastic has been found desirable in view of its characteristic smooth surface that typically does not snag a coil-type implant.

It is important that the filter remain securely abutted against the proximal end or inlet of tube 52. In the preferred embodiment, the filter is cylindrical and press fit into recess 56; it has a diameter that provides an interference preferably of about 0.003–0.010 inch with the inner wall of hub 50 that forms recess 56. In the embodiment shown in FIG. 4A, that inner wall has a cylindrical configuration.

Other interference designs also may be used. For example, the inner wall configuration of hub 50 may be star shaped. One such configuration is shown in FIG. 4B. The star configuration generally facilitates manufacturability. It has less sensitivity to filter and hub tolerances which are important to provide an effective press fit. It also permits fluid flow through radial channels 51 rendering filter porosity sensitivity less important.

Returning to FIG. 4A, tubular member 52 has a proximal end, which is secured within hub recess 58, and a distal end adapted for being releasably secured within an inlet of sidearm 6, or in the alternative, with a conventional inlet hub of the catheter 4. Tubular member 52 includes a passage 62 sized to contain an occlusive device of the present invention in a linear configuration. Thus, passage 62 is sized to restrain the secondary structure of the occlusion device to a diameter essentially equal to that of the proximal section of the occlusion device.

More specifically, the inner diameter of passage 62 is slightly greater than the outer diameter of the proximal nonpreformed portion of the occlusion device so that the secondary windings can expand a very small amount to reduce the friction between the inner wall of tubular member 52 and section 27 of the device. This enhances uniform displacement of the device through the introducer cartridge (the catheter lumen is similarly sized to enhance discharge of the device). According to the embodiment illustrated in FIG. 4A, a removable cap 64 is provided on the distal end of tubular member 52. Cap 64 is constructed to maintain the implant in tubular member 52 during shipping or handling prior to use. Cap 64 also is preferably constructed to facilitate the removal of air from the introducer cartridge without implant discharge prior to use.

In the preferred embodiment, cap 64 includes a discharge port or opening 64a and a blocking member or filter 65 disposed therein. The blocking member 65 is sized so as not to pass through opening 64a, preferably has a cylindrical form and preferably comprises a porous plastic material as described above in conjunction with filter 61. In addition, tubular member 52, blocking member 65 and opening 64a preferably are coaxial. Cap 64 further preferably comprises plastic, such as polyethylene or polypropylene, and is configured to form a press fit onto the distal end of tubular member 52 and with blocking member 65. In the preferred embodiment, the inner wall of the cap is formed with a plurality of longitudinally and radially extending, circumferentially spaced ribs 67 (FIGS. 4A and C) that form a press fit with tubular member 52 and blocking member or filter 64. The ribs can be configured so that they are somewhat crushed against tubular member 52 when the cap is press fit on the tubular member as would be apparent to one of ordinary skill. The cap may be heated and positioned on a mandrel with negative regions to form the ribs or by other conventional techniques such as injection molding. Other cap constructions also may be used. For example, the cap may comprise porous plastic.

Although a particular introducer cartridge has been described, other introducer cartridges having varied configurations to accommodate the needs of particular syringes or catheters, for example, can be used as would be apparent to one of ordinary skill.

Merely to exemplify the operation of the invention, the following example in which a vaso-occlusive device constructed according to the embodiment illustrated in FIGS. 2A & B is provided. This example is provided for illustrative purposes and is not intended to limit the invention. Vaso-occlusive device 20 is delivered through a catheter, e.g., catheter 4. Catheter 4 generally comprises an elongate tubular member having proximal and distal end portions 4a and 4b. The catheter is preferably between about 50–300 cm in length, and typically between about 60–200 cm in length. The catheter also is designed for accessing a vessel site at which, for example, vaso-occlusion is desired. For example, the vessel site can be within a small diameter vessel having 1–5 mm lumen diameter and accessible by way of a tortuous vessel path which may involve sharp vessel turns and multiple vessel branches. In this case, the catheter preferably has a small diameter, flexible construction with a lumen diameter of less than about 0.8 mm and preferably between about 0.5 to 0.7 mm. Catheters of this type, which are typically used for accessing deep brain vascular sites, are commercially available.

The catheter is inserted through a vessel lumen to the site to be occluded (e.g., a vascular malformation, arteriovenous fistula or mininginoma type tumor). Conventional catheter insertion and navigational procedures involving a guidewire or flow-directed means (such as disclosed in U.S. Pat. No. 5,336,205) may be used to access the site with the catheter. Thus, although not shown, catheter 4 may include a guidewire usable therewith to guide the distal end of the catheter toward the desired or selected occlusion site. Guidewires of this type are commercially available, and generally include an elongate wire having a tapered, wire-wound distal end region which is adapted to be advanced through a tortuous vessel path, with the catheter being moved axially along the advanced guidewire.

Once the distal end of the catheter is positioned at the selected site (its location may be determined by a coating at the distal end of the catheter with a radiopaque material or otherwise affixing such a material to the distal end of the catheter or incorporating such a material into the distal end of the catheter), the catheter is cleared. For example, if a guidewire has been used to position the catheter, it is withdrawn from within the catheter.

Prior to delivering a vaso-occlusive device in vivo, a syringe (e.g., a 3 cc syringe) is attached to hub 50 of the introducer cartridge with cap 64 positioned on the distal end of tubular member 52. Human compatible fluid, such as saline, is injected slowly from the syringe and through hub 50 and tubular member 52 to purge all the air from the introducer cartridge. The distal end of the tubular member 52, including the cap 64, is then submerged in a saline solution filled container or basin. Alternatively, cap 64 can be submerged in the saline solution during the purging step. The syringe plunger is then pulled back such that the occlusive device is urged proximally away from cap 64 to prevent the device from exiting the introducer cartridge prematurely when removing the cap. The introducer cartridge is placed in a horizontal position for inspection. If air remains in the introducer cartridge, the purging steps described above are repeated. If the air has been completely purged from the introducer cartridge, cap 64 is removed and the introducer cartridge is coupled to the proximal end of the catheter via sidearm 6.

The plunger in syringe 12, which preferably is loaded with a saline solution as described above, is slowly pushed down to displace the vaso-occlusion device from introducer cartridge 8 down through catheter 4 to the injection site (FIG. 5). As the plunger continues to be pushed inwardly, portion 27 of distal portion 26 is discharged from the catheter where it returns to its secondary configuration (FIG. 6). As the fluid from syringe 12 continues to force vaso-occlusive device 20 from the catheter, the proximal portion is discharged from the catheter and piles against, around and/or in portion 27 in a random fashion to form an occlusive mass. It is believed that since the proximal portion of the vaso-occlusion device has a significantly lower flow resistance configuration than that of the secondary structure in the distal portion, the discharge fluid accelerates the proximal portion through the blood toward secondary windings 28 to form the occlusive mass (FIGS. 7 and 8).

The flexibility of the proximal portion described above allows the proximal portion to fold over the secondary windings 28 and remain in that position without the need for external forces or other restraining mechanisms. The proximal portion can, however, become intertwined with secondary windings 28 and other portions of the proximal portion.

Figure 8:
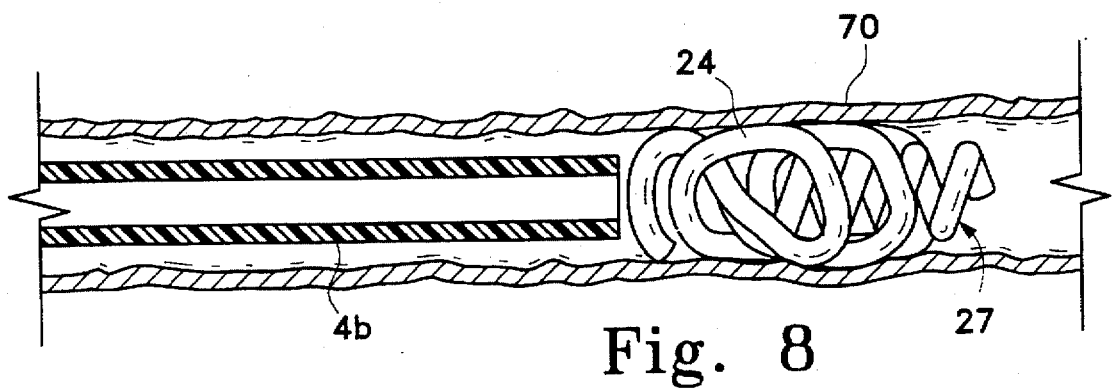
FIG. 8 shows the configuration of the occlusion device of FIG. 7 anchored in position after ejection.

As the proximal portion balls up in a dense mass, it expands volumetrically, frictionally engages the inner walls of vessel 70 and anchors the vaso-occlusion device in that position as shown in FIG. 8. The flexibility of the device allows it to ball up as desired under a hydraulic pressure of about 50 to 150 psi. Occlusive masses volumetrically filling about 40–75% of an imaginary sphere that surrounds the mass can be achieved. This high volume packing efficiency facilitates very high occlusion rates.

Figure 9:
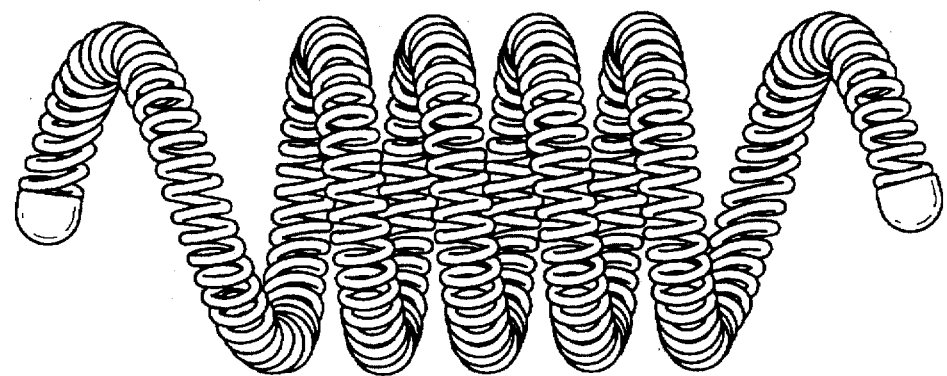
FIG. 9 is a side view of an auxilliary occlusion device.

After the vaso-occlusion device is positioned and/or anchored at the desired site, additional devices may be injected by exchanging the empty introducer cartridge with another loaded with another occlusion device. The additional (secondary) occlusion devices may be configured as described above or they may be configured otherwise. For example, the secondary occlusion devices may comprise a coil configured with a generally uniform helical secondary shape such as shown in FIG. 9 or a straight coil with no secondary shape. It is believed that the secondary coils add to the mass of the first positioned occlusion device and facilitate or enhance anchoring the first positioned occlusion device in place.

Additionally, the method of the present invention may include the step of introducing polymer resins, such as cyanoacrylate resins (particularly n-butylcyanoacrylate) to the intended site after the inventive coils, braids, and/or chains are in place. That is, the inventive devices form a substrate for these tissue adhesives, or particulate embolization materials such as microparticles of polyvinyl alcohol foam, or various chemotherapeutic agents.

Throughout this application, various publications, patents and patent applications are referred to by an identifying citation. The disclosures of these publications, patents and published patent applications are hereby incorporated by referenced into this application.

The above is a detailed description of particular embodiments of the invention. It is recognized that departures from the disclosed embodiments may be made within the scope of the invention and that obvious modifications will occur to a person skilled in the art. The full scope of the invention is set out in the claims that follow and their equivalents. Accordingly, the claims and specification should not be construed to unduly narrow the full scope of protection to which the invention is entitled.

What is claimed is:

1. An occlusive implant comprising an elongated member having a proximal portion and a distal portion, said proximal portion having a flexibility of at least a 20° deflection from horizontal under its own weight when a 1 cm section of said proximal portion having an unrestrained free end is horizontally supported and said deflection is measured at said free end, at least a portion of said distal portion having a first configuration when restrained in a first state within a catheter and a second different configuration when in an unrestrained second state, said proximal portion therefore capable of maintaining the first configuration both when restrained and when unrestrained, said distal portion second configuration having a flow resistance substantially greater than that of said first configuration proximal portion.

2. The implant of claim 1 wherein said proximal and distal portions are contiguous and can be arranged so that the flow resistance of the elongated member is essentially uniform along its length.

3. The implant of claim 1 wherein said proximal and distal portions can be arranged to have a common longitudinal axis and diameter.

4. The implant of claim 1 wherein said proximal portion has a generally uniform diameter along its length and said distal portion has a diameter when in its second configuration of at least about twice that of said proximal portion diameter.

5. The implant of claim 1 wherein said proximal portion assumes a random configuration when unrestrained within a catheter.

6. The implant of claim 5 wherein said distal portion substantially maintains its preformed configuration when unrestrained within a catheter.

7. The implant of claim 1 wherein said proximal portion forms at least the same length as said distal portion second configuration.

8. The implant of claim 1 wherein said distal portion second configuration is generally helical.

9. The implant of claim 1 wherein said implant is an embolic device.

10. The implant of claim 9 wherein said device comprises a coil.

11. The implant of claim 10 wherein said coil comprises a filament formed into multiple windings, said filament being ≦ about 1 mil (0.001 inches) in diameter.

12. A vaso-occlusive device comprising proximal and distal portions, said vaso-occlusive device being of a size, shape, and material such that said proximal portion has a flexibility of at least a 20° deflection from horizontal under its own weight when a 1 cm section of said proximal portion having an unrestrained free end is horizontally supported and said deflection is measured at said free end and has a first configuration both when restrained and when unrestrained, at least a portion of said distal portion having said first configuration when in a first state and a second preformed configuration different than the first state when in a relaxed state.

13. The device of claim 12 wherein said proximal portion has a length that is at least about 100% the length of said portion of the distal portion when the latter is in said second state.

14. An introducer cartridge comprising:
a first portion having a passage formed therethrough and a region adapted for coupling to a catheter;
an implant disposed in said passage;
a second portion having a recess formed therein and in fluid communication with said passage; and
a porous plastic blocking member having a porosity in the range of about 50 μ to 100 μ positioned in said recess adjacent to said passage.

15. The introducer cartridge of claim 14 wherein said blocking member is configured for preventing displacement of said implant thereby.

16. The introducer cartridge of claim 14 wherein said first portion includes an outlet and the introducer cartridge includes a cap removably coupled to said outlet.

17. The introducer cartridge of claim 16 wherein said cap includes at least one perforate portion for discharging fluid therethrough.

18. The introducer cartridge of claim 16 further including a filter disposed in said cap.

19. The introducer cartridge of claim 18 wherein said cap includes an opening formed therethrough and in fluid communication with said filter.

20. The introducer cartridge of claim 19 wherein the filter disposed in said cap comprises porous plastic.

21. A vaso-occlusive device cartridge assembly comprising: a vaso-occlusive device having first and second regions, said first region having a first configuration both when restrained and when unrestrained, said first region having a flexibility of at least a 20° deflection from horizontal under its own weight when a 1 cm section of said first region having an unrestrained free end is horizontally supported and said deflection is measured at said free end, and said second region having said first configuration when restrained and a secondary relaxed preformed configuration, said second region secondary configuration being different than the second region first configuration and having a flow resistance substantially greater than said first configuration and wherein said first region has an axial length that is at least about 100% of the axial length of the secondary configuration of said second region;
a tube that surrounds and restrains said device in a generally linear configuration, said tube having a proximal end to which said first region is adjacent and a distal end; and
an adapter coupled to said proximal end of said tube for coupling a fluid source to said tube.

22. The assembly of claim 21 wherein said first region has an axial length that is at least about 100% the axial length of the secondary configuration of said second region.

23. The assembly of claim 21 further including a blocking member, said tube defining a passage in which said device is disposed, said adapter having a recess formed therein and fluidly coupled to said passage, and said blocking member being positioned in said recess adjacent to said passage and sized for preventing displacement of said device thereby.

24. The assembly of claim 23 wherein said blocking member is perforate.

25. The assembly of claim 23 wherein said blocking member comprises a filter.

26. An occlusive implant comprising an elongated member having a proximal portion and a distal portion, said occlusive implant being of a size, shape, and material such that said proximal portion having a flexibility of at least a 20° deflection from horizontal under its own weight when a 1 cm section of said proximal portion having an unrestrained free end is horizontally supported and said deflection is measured at said free end and wherein said proximal portion has a first configuration both when restrained and when unrestrained, at least a portion of said distal portion being preformed to have said first configuration when restrained in a first state within a catheter and a second different configuration when in an unrestrained second state, said distal portion second configuration having a flow resistance substantially greater than that of said first configuration proximal portion and wherein the proximal portion first configuration has a length at least 100% of the distal portion second configuration length.

27. The implant of claim 26 wherein said proximal and distal portions are contiguous and can be arranged so that the flow resistance of the elongated member is essentially uniform along its length.

28. The implant of claim 26 wherein said proximal and distal portions can be arranged to have a common longitudinal axis and diameter.

29. The implant of claim 26 wherein said proximal portion has a generally uniform diameter along its length and said distal portion has a diameter when in its second configuration of at least about twice that of said proximal portion diameter.

30. The implant of claim 26 wherein said proximal portion assumes a random configuration when generally unrestrained.

31. The implant of claim 30 wherein said distal portion substantially maintains its preformed configuration when generally unrestrained.

32. The implant of claim 26 wherein said proximal portion forms at least the same length as said distal portion second configuration.

33. The implant of claim 26 wherein said distal portion second configuration is generally helical.

34. The implant of claim 26 wherein said implant is an embolic device.

35. The implant of claim 34 wherein said device comprises a coil.

36. The implant of claim 35 wherein said coil comprises a filament formed into multiple windings, said filament being $\leq$ about 1 mil (0.001 inches) in diameter.

* * * * *

UNITED STATES PATENT AND TRADEMARK OFFICE
CERTIFICATE OF CORRECTION

PATENT NO. : 5,669,931
DATED : September 23, 1997
INVENTOR(S) : David Kupiecki et al.

It is certified that error appears in the above-identified patent and that said Letters Patent is hereby corrected as shown below:

*column 1, line 27*: change "in vivo" to -- *in vivo* --.

*column 3, line 11*: change "in vivo" to -- *in vivo* --.

*column 6, line 14*: change "in vivo" to -- *in vivo* --.

*column 7, line 49*: change "61*a*" to -- 61a --.

*column 7, line 50*: change "61*b*" to -- 61b --.

*column 8, line 52*: change "64*a*" to -- 64a --.

*column 8, line 54*: change "64*a*" to --64a --.

*column 8, line 57*: change "64*a*" to --64a --.

*column 9, line 20*: change "4*a*" to -- 4a --.

*column 9, line 21* change "4*b*" to -- 4b --.

*column 9, line 56*: change "in vivo" to -- *in vivo* --.

Signed and Sealed this

Sixteenth Day of December, 1997

Attest:

Attesting Officer

BRUCE LEHMAN

Commissioner of Patents and Trademarks